United States Patent [19]
Avraham et al.

[11] Patent Number: 5,981,201
[45] Date of Patent: Nov. 9, 1999

[54] METHODS OF DETECTION AND TREATMENT OF BREAST CANCER

[75] Inventors: Hava Avraham; Jerome E. Groopman, both of Brookline, Mass.

[73] Assignee: Beth Israel Deaconess Medical Center, Boston, Mass.

[21] Appl. No.: 08/876,882

[22] Filed: Jun. 16, 1997

Related U.S. Application Data

[60] Provisional application No. 60/035,228, Jan. 8, 1997.

[51] Int. Cl.$^6$ ............... G01N 33/573; A61K 39/395; C12N 5/06; C07K 16/00
[52] U.S. Cl. ............... 435/7.4; 424/9.6; 424/130.1; 424/138.1; 424/139.1; 424/141.1; 424/146.1; 435/330; 436/512; 530/387.1; 530/387.7; 530/389.9
[58] Field of Search ............... 424/9.6, 130.1, 424/132.1, 138.1, 139.1; 435/4; 436/512, 547; 530/387.1, 387.9, 387.7, 388.15

[56] References Cited

PUBLICATIONS

Zrihan–Licht S. et al., "Csk homologous kinase, a novel signaling molecule, directly associates with the activated ErbB–2 receptor in breast cancer cells and inhibits their proliferation." *J Biol. Chem.* 273:4065–4072 (1998).
Avraham, S. et al., "Structural and Functional Studies of the Intracellular Tyrosine Kinase MATK Gene and its Translated Product," *J. Biol. Chem.* 270:1833–1842 (1995).
Beerli, R.R. et al., "Neu Differentiation Factor Activation of ErbB–3 and ErbB–4 Is Cell Specific and Displays a Differential Requirement for ErbB–2," *Mol. Cell. Biol.* 15:6496–6505 (1995).
Ben–Levy, R. et al., "An Oncogenic Point Mutation Confers High Affinity Ligand Binding to the neu Receptor," *J. Biol. Chem.* 267:17304–17313 (1992).
Ben–Levy, R. et al., "A single autophosphorylation site confers oncogenicity to the Neu/ErbB–2 receptor and enables coupling to the MAP kinase pathway," *EMBO J.* 13:3302–3311 (1994).
Bennett, B.D. et al., "Identification and Characterization of a Novel Tyrosine Kinase From Megakaryocyes," *J. Biol. Chem.* 269:1068–1074 (1994).
Bishop, J.M., "Cancer: the rise of the genetic paradigm," *Genes & Dev.* 9:1309–1315 (1995).
Chow, L.M.L. et al., "Ntk: A Csk–related protein–tyrosine kinase expressed in brain and T lymphocytes," *Proc. Natl. Acad. Sci. USA* 91:4975–4979 (1994).
Cohen, B.D. et al., "HER4–mediated Biological and Biochemical Properties in NIH 3T3 Cells," *J. Biol. Chem.* 271:4813–4818 (1996).
Earp, H.S. et al., "Heterodimerization and functional interaction between EGF receptor family members: A new signaling paradigm with implications for breast cancer research," *Breast Cancer Research and Treatment* 35:115–132 (1995).

Graus–Porta, D. et al., "Single–Chain Antibody–Mediated Intracellular Retention of ErbB–2 Impairs Neu Differentiation Factor and Epidermal Growth Factor Signaling," *Mol. Cell. Biol.* 15:1182–1191 (1995).
Hamaguchi, I. et al., "Characterization of mouse non–receptor tyrosine kinase gene, HYL," *Oncogene* 9:3371–3374 (1994).
Hennipman, A. et al., "Tyrosine Kinase Activity in Breast Cancer, Benign Breast Disease, and Normal Breast Tissue," *Cancer Res.* 49:516–521 (1989).
Jhun, B.H. et al., "The MATK Tyrosine Kinase Interacts in a Specific and SH2–dependent Manner with c–Kit," *J. Biol. Chem.* 270:9661–9666 (1995).
Klages, S. et al., "Ctk: A protein–tyrosine kinase related to Csk that defines an enzyme family," *Proc. Natl. Acad. Sci. USA* 91:2597–2601 (1994).
Kuo, S.S. et al., "Identification and Characterization of Batk, a Predominantly Brain–Specific Non–Receptor Protein Tyrosine Kinase Related to Csk," *J. Neurosci. Res.* 38:705–715 (1994).
Levi, A.D.O. et al., "The Influence of Heregulins on Human Schwann Cell Proliferation," *J. Neurosci.* 15:1329–1340 (1995).
Luttrell, D.K. et al., "Involvement of $pp60^{c-src}$ with two major signaling pathways in human breast cancer," *Proc. Natl. Acad. Sci. USA* 91:83–87 (1994).
McVicar, D.W. et al., "Molecular cloning of lsk, a carboxyl–terminase src Kinase (csk) related gene, expressed in leukocytes," *Oncogene* 9:2037–2044 (1994).
Musso, T. et al., "IL–4 and IL–13 Induce Lsk, a Csk–like Tyrosine Kinase, in Human Monocytes," *J. Exp. Med.* 180:2383–2388 (1994).
Olsson, H. et al., "Her–2/neu and INT2 Proto–oncogene Amplification in Malignant Breast Tumors in Relation to Reproductive Factors and Exposure to Exogenous Hormones," *J. Natl. Cancer Instit.* 83:1483–1487 (1991).
Ottenhoff–Kalff, A.E. et al. "Characterization of Protein Tyrosine Kinases from Human Breast Cancer: Involvement of the c–src Oncogene Product," *Cancer Res.* 52:4773–4778 (1992).
Peles, E. et al., "Regulated Coupling of the Neu Receptor to Phosphatidylinositol 3'–kinase and its Release by Oncogenic Activation," *J. Biol. Chem.* 267:12266–12274 (1992).
Price, D. et al., "Characterization of Interaction of the Megakaryocyte Associated Tyrosine Kinase, MATK, with the c–kit Receptor," *Blood* 86(supp):284a (abstract #1122) (1995).
Price, D.J. et al., "Direct Association of Csk Homologous Kinase (CHK) with the Diphosphorylated Site $Tyr^{568/570}$ of the Activated c–KIT in Megakaryocytes," *J. Biol. Chem.* 272:5915–5920 (1997).

(List continued on next page.)

*Primary Examiner*—Paula K. Hutzell
*Assistant Examiner*—Timothy A. Worrall
*Attorney, Agent, or Firm*—Hamilton, Brook, Smith & Reynolds, P.C.

[57] ABSTRACT

Novel methods of detecting and treating breast cancer are described.

3 Claims, 5 Drawing Sheets

OTHER PUBLICATIONS

Sakano, S. et al., "Molecular cloning of a novel non–receptor tyrosine kinase, HYL (hematopoietic consensus tyrosine–lacking kinase)," *Oncogene* 9:1155–1161 (1994).

Slamon, D.J. et al., "Studies of the HER–2/neu Proto–oncogene in Human Breast and Ovarian Cancer," *Science 244*:707–712 (1989).

Soule, H.D. et al., "Isolation and Characterization of a Spontaneously Immortalized Human Breast Epithelial Cell Line, MCF–10," *Cancer Res. 50*:6075–6086 (1990).

Taylor, S.J. et al., "Src and the control of cell division," *BioEssays 18*:9–11 (1996).

Wen, D. et al., "Neu Differentiation Factor: A Transmembrane Glycoprotein Containing an EGF Domain and an Immunoglobulin Homology Unit," *Cell 69*:559–572 (1992).

Zrihan–Licht, S et al., "Association of Csk–homologous Kinase (CHK) (formerly MATK) with HER–2/ErbB–2 in Breast Cancer Cells," *J. Biol. Chem. 272*:1856–1863 (1997).

Zwijsen, R.M.L. et al., "Cyclin D1 Triggers Autonomous Growth of Breast Cancer Cells by Governing Cell Cycle Exit," *Mol. Cell. Biol. 16*:2554–2560 (1996).

PT: CHK-SH2
WB: PY20

IP: ErbB-2
WB: PY20

PT: CHK-SH2
WB: ErbB-2

IP: ErbB-2
WB: ErbB-2

FIG. 2A

```
   1 GGAGCAACTCGCTCCAAGTTGTGCAGCCGGGACCGCCCTCGGGGTGTGCAGCCGGCTCCGCGGAGGCCCTCCTCTGGGGCGGGGGCGGCTCGG
  96 GGGCGCCCCCTGAGCAGCAGAAAACAGGAAGAACCAGGCTCGGTCCAGTGGCCACCCAGGCTCCCTACCTCCTGTGCCAGCCGCTCCTGGCAGGC
                                                                           MetAlaGlyArgGlySerLeuVal
 191 CATTCCCAGCGTCCCCGACTGTGACCACTTGCTGACTGGTGCCTCAGTGTTTCCTCTGGGGGCGATGGCGGGGGGAGGCTCTCTGGT
                                                                    10                            40
     SerTrpArgAlaPheHisGlyCysAspSerAlaGluGluLeuProArgPheLeuProArgValSerProPheArgAlaTrpHisProProValSerAla
 286 TTCCTGGCGGGCATTTCACGGCTGTGATTCTGCTGAGGAACTTCCCGGGTGAGCCCTTCCCGAGCCTGGCACCCCCCTCCCGTCTCAG
                                20                                     50                     70
     ArgMetProThrArgArgTrpAlaProGlyThrGlnCysIleThrLysCysGluHisThrArgProLysProGlyLeuAlaPheArgLys
 381 CCAGGATGCCAACGAGGCGTGGGCCCCGGCCACCCAGTGTATCACCAAATGCGAGCACACCCGCCCCAAGCCAGGGAGCTGGCCTTCCGCAAG
                                 80                                     90                     100
     GlyAspValValThrIleLeuGluAlaCysGluAsnLysSerTrpTyrArgValLysHisHisThrSerGlyGlnGluGlyLeuLeuAlaAlaGly
 476 GGCGACGTGGTCACCATCCTGGAGGCCTGTGAGAACAAGAGCTGGTACCGCGTCAAGCACCACAGTGGACAGGAGGGCCTGCTGGCAGCTGG
                                  110                                    120                    130
     AlaLeuArgAspGlyGluAlaLeuSerAlaAspProLysLeuSerLeuMetProTrpPheHisLysIleSerGlyGlnAlaValGlnGln
 571 GCGCTGCGGGACGGGGAGGCCCTCTCCGCAGACCCCAAGCTCAGCCTCATGCCGTGGTTCCACGGGAAGATCTCGGGCCAGGAGGCTGTCCAGC
                                   140                                    150                    160
     LeuGlnProProGluAspGlyLeuPheLeuValArgGluSerAlaArgHisProGlyAspTyrValLeuCysValSerPheGlyArgAspVal
 666 AGCTGCAGCCTCCCGAGGATGGCCTGTTCCTGGTGCGGGAGTCCGCGCGCCACCCCGGCGACTACGTCCTGTGCGTGAGCTTTGGCCGCGACGTC
                                   170                                    180                    190
     IleHisTyrArgValLeuHisArgAspGlyHisLeuThrIleAspGluAlaValPhePheCysAsnLeuMetAspMetValGluHisTyrSerLys
 761 ATCCACTACCGCGTGCTGCACCGCGACGGCCACCTCACAATCGATGAGGCCGTGTTCTTCTGCAACCTCATGGACATGGTGGAGCATTACAGCAA
                                    200                                    210                   230
     AspLysGlyAlaIleCysThrLysLeuValArgProLysArgLysHisGlyThrLysSerAlaGluLeuAlaArgAlaArgGlyTrpLeuLeu
 856 GGACAAGGGCGCTATCTGCACCAAGCTGGTGAGACCCAAAGCGAAACACGGCACCAAGAGCGCCGAGCTGGCCAGGGCCCGGGGCTGGTTAC
                                    220                                    250                    260
     AsnLeuGlnHisLeuThrLeuGlyAlaGlnIleGlyPheGlyAlaValLeuGlnGlyTyrLeuGlyLysValAlaVal
 951 TGAACCTGCAGCATTTGACATTGGGAGCACAGATCGGAGAGGGAGAGTTTGAGCTGTCCTGCAGGTGAGTACCTGGCAAAAGGTGGCCGTG
```

FIG. 2B

```
                                                          270                                 280                                 290
      LysAsnIleLysCysAspValThrAlaGlnAlaPheLeuAspGluThrLysMetThrLysMetGlnHisGluAsnLeuValArgLeuLeuGly
1046  AAGAATATCAAGTGTGATGTGACAGCCCAGGCCTTCCTGGACGAGACGGCCGTCATGACGAAGATGCAACACGAGAACCTGGTGCGTCTCCTGGG
                  300                                 310                                 320
      ValIleLeuHisGlnGlyLeuTyrIleValMetGluHisValSerLysGlyAsnLeuValAsnPheLeuArgThrArgGlyAlaLeuValAsn
1141  CGTGATCCTGCACCAGGGCCTGTACATTGTCATGGAGCACGTGAGCAAGGGCAACTTGTGAACTTTCTGCGGACCCGGGGTCGAGCCCTCGTGA
                  330                                 340                                 350
      ThrAlaGlnLeuLeuGlnPheSerLeuHisValAlaGlyGlyMetGluTyrLeuGluSerLysLysLeuValHisArgAspLeuAlaAlaArg
1236  ACACCGCTCAGCTCCTGCAGTTTTCTCTGCACGTGGCCGAGGGCATGGAGTACCTGGAGAGCAAGAAGCTTGTGCACCGCGACCTGGCCGCCGC
                  360                                 370                                 380
      AsnIleLeuValSerGluAspPheLeuValAlaLaLysValSerAspPheGlyLeuAlaLeuAlaLysAlaGluArgLysGlyLeuAspSerSerArgLeuProVal
1331  AACATCCTGGTCTCAGAGGACTTTCTGGTGGCCAAGGTCAGCGACTTTGGCCTGGCCAAAGCCGAGCGAAGGGCTAGACTCAAGCCGGCTGCCCGT
                  390                                 400                                 410                          420
      LysTrpThrAlaProGluAlaLeuLysHisGlyThrSerLysPheSerAspValTrpSerPheGlyValLeuLeuTrpGluValPheSerTyrGly
1426  CAAGTGGACGGCGCCCAGGCTCCAAACACGGGTCTCACCAGCAAGTCGGATGTCTGGAGTTTTGGGGTGCTGCTCTGGGAGGTCTTCTCATATG
                  430                                 440                                 450
      ArgAlaProTyrProLysMetSerLeuLysGluValSerGluAlaValGluLysGlyTyrArgMetGluProProGluGlyCysProGlyPro
1521  GACGGGCTCCGTACCCTAAAATGTCACTGAAAGAGGTGTCGGAGGCCGTGGAGAAGGGGTACCGCATGGAACCCCCCGAGGGCTGTCCAGGCCCC
                  460                                 470                                 480
      ValHisValLeuMetSerSerCysTrpGluAlaAlaGluProProAlaGlyHisProSerAlaAsnTrpProArgSerProGlySerTyrAlaValVal
1616  GTGCACGTCCTCATGAGCAGCTGCTGGGAGGCAGAGCCCCCGGCCGGCCACCCTTCCGCAAACTGCCGAGAAGCTGGCCCCGGGAGCTACGCAGT
                  490                                 500                                 510
      GlnValProGlnProSerGlnGlyArgThrProThrValHisLeuAlaProLysProGlyAlaLeuThrProProGlyProTrpProGln
1711  GCAGGTGCCCCAGCCTCCCAGGGCAGGACGCCCACGGTCCACCTGCCCCCCGAAGCCAGGACCCCGACCCGGTGGCCCTTGGCCCC
                  520
      ArgThrGluArgValGluSerAlaAlaTrpGlyHis
1806  AGAGGACCGAGAGAGTGGAGAGTGCGGCGTGGGGCACTGACCAGGCCCAAGGAGGTCCAGGCGGGCAAGTCATCCTCCTGGTGCCCACAGCAG
1901  GGGCTGGCCCACGTAGGGGCTCTGGGGCCCGTGGACACCCCAGACCTGCGAAGGATGATCGCCCGATAAAGACGATTCTAAGG
```

FIG. 3

```
1                     21         PTK 1/3 PRIMERS              41
5' ggatccattcacagagacctagcagcacgcaacatcctggtctcagaggacctggtaacc
    G  S  I  H  R  D  L  A  A  R  N  I  L  V  S  E  D  L  V  T 61                    81                                    101
aaggtcagcgactttggcctggcccaaagccgagcggaagggctagactcaagccggctg
 K  V  S  D  F  G  L  A  K  A  E  R  K  G  L  D  S  S  R  L 121       PTKKW PRIMER      141
cccgtcaaatggatggctcccgaattc 3'
 P  V  K  W  M  A  P  E  F
```

METHODS OF DETECTION AND TREATMENT OF BREAST CANCER

RELATED APPLICATIONS

This application claims priority to pending Provisional application Ser. No. 60/035,228, filed Jan. 8, 1997, the content of which is incorporated herein by reference in its entirety.

GOVERNMENT SUPPORT

This invention described herein was supported in whole or part by the National Institutes of Health Grant No. HL51456-02. The United States Government has certain rights in this invention.

BACKGROUND OF THE INVENTION

Breast cancer is the second leading cause of cancer death among women in the United States and is the leading cause of death among women aged 30–70. (Abeloff, M. D., Curr. Opin. Oncol., 8:447–448 (1996)). The inheritance of germline mutations in autosomal dominant susceptibility genes appears to be responsible for 5–10% of all breast cancer cases (Fitzgerald, M. G., et al., New Engl. J. Med., 334:143–149 (1996)), and up to 36% of the cases diagnosed before age 30. BRCA1 was the first isolated breast cancer susceptibility gene (Langston, A. A., et al., New Engl. J. Med., 334:137–142 (1996); Couch, F. J. and Weber, B. L., Hum. Mutat., 8:8–18 (1996)) and mutations in BRCA1 alone account for approximately 45% of the families with high incidence of breast and ovarian cancer (Chen, Y. M., et al., Science, 272:125–126 (1996); Sully, R., et al., Science, 272:123–126 (1996)). In addition, a second breast cancer susceptibility gene, BRCA2, has been isolated recently (Wooster, R., et al., Nature, 378:789–792 (1995); Tavtigian, S. V., et al., Nat. Genet., 12:333–337 (1996)).

However, the majority of breast carcinomas appear to be sporadic and have a complex accumulation of molecular and cellular abnormalities that constitute the malignant phenotype. A number of somatic gene alterations, such as loss of expression of specific tumor suppressor genes, have been found to occur in primary human breast tumors (Borg, A., et al., Cancer Res., 52:2991–2994 (1992); Eeles, R. A., et al., Cancer Surveys, 25:101–124 (1995)). Additionally, there is considerable evidence that genetic alterations in growth factor signaling pathways can contribute to human breast malignancies. In this regard, activation of different proto-oncogenes has been found in primary breast tumor (Berns, E. M., et al., Cancer Res., 52:1036–1039 (1992); Borg, A., et al., Brit. J. Cancer, 63:136–142 (1991); Gullick, W. J., et al., Brit. J. Cancer, 63:434–438 (1991)). Thus, there is considerable importance in identifying, at a molecular level, factors that contribute to the progression from normal growth towards malignancy.

SUMMARY OF THE INVENTION

The present invention relates to the demonstration that a cytoplasmic protein tyrosine kinase, Csk Homologous Kinase or CHK, is expressed in human breast cancer, but not in adjacent normal breast tissue. Specifically, the present invention relates to methods of detecting the presence of cancer in mammalian breast tissue by the detection of the protein tyrosine kinase CHK, or the detection of nucleic acids encoding the CHK in mammalian tissue, specifically breast tissue. The detection of CHK in breast tissue is indicative of cancer.

The presence of CHK in breast tissue can be determined by detecting the expression of CHK protein, or a protein fragment, in breast tissue samples obtained from the mammal. For example, biopsy tissue can be obtained from the mammal, fixed in a suitable medium and contacted with anti-CHK antibodies, for example rabbit anti-CHK, which specifically bind to the CHK protein if it is present in the tissue sample. The anti-CHK antibody can itself be detectably labeled, or a detectably labeled second antibody, for example, peroxidase-conjugated mouse anti-rabbit antibody, can be used.

The presence of CHK in breast tissue can also be detected using an immunoblot (e.g., Northern blot) assay. For example, tissue can be obtained from the mammal and a cell lysate prepared which contains proteins released from the tissue cells. The lysate proteins can be separated by electrophetic means, such as by size by SDS polyacrylamide gel electrophoresis, and contacted with anti-CHK antibody which specifically binds to CHK if it is present in the lysate. Again, the anti-CHK antibody can be detectably labeled, or a detectably labeled second antibody can be used. Alternatively, CHK protein present in a cell lysate can be detected by enzyme linked immunosorbent assay (ELISA), radioimmunoassay (RIA) or other immunoassays.

The presence of CHK in breast tissue can also be determined by detecting the presence of a nucleic acid sequence encoding all, or a portion, of the CHK protein. The nucleic acid can be DNA or RNA. For example, genomic DNA, cDNA or RNA can be obtained from a sample of breast tissue and contacted with a polynucleotide (a nucleic acid probe) that forms a stable hybrid with the nucleic acid sequence encoding CHK. The probe can be detectably labeled. The DNA or RNA obtained from the mammal can be amplified prior to assay, for example using the polymerase chain reaction (PCR) or the ligase chain reaction (LCR), using specific nucleic acid primers. Primers useful to amplify the CHK nucleic acid specifically hybridize to the CHK nucleic acid or to nucleic acid sequence that flanks the target CHK nucleic acid sequence region.

Overexpression of the receptor tyrosine kinase, ErbB-2 (also termed neu/HER-2) has been associated with the development of breast cancer. (Slamon, D. J., et al., Science, 244:707–712 (1989); Olsson, H., et al., J. Natl. Cancer Instit., 83:1483–1487 (1991)). A common pathway linking the activation mechanisms in ErbB-2 amplification in breast cancer is increased tyrosine kinase activity which leads to cellular transformation. The abundance of ErbB-2 receptors and their ligands (e.g., heregulin or HGR) in breast cancer points to a functional role in the pathogenesis of this malignancy. As demonstrated herein, CHK specifically interacts with activated ErbB-2 upon HGR stimulation and results described herein suggest that CHK functions as a negative regulator of ErbB-2 mediated mitogenic signaling.

Accordingly, the present invention also encompasses methods of inhibiting breast cancer cell growth (also referred to herein as neoplastic cell growth), specifically ErbB-2 mediated neoplastic cell growth, by supplying CHK to cancer cells. For example, CHK protein, peptide or a biologically active fragment thereof, or a CHK analog or derivative, can be supplied to mammalian breast tissue which is abnormal, e.g., neoplastic, or at risk of becoming abnormal. The CHK protein can be supplied to the target breast tissue by introducing into target cells a liposome preparation that contains CHK. Specifically encompassed by this invention is the topical application of such liposomes in a cream or ointment.

Alternatively, CHK can be supplied to the target tissue by introducing a nucleic acid sequence encoding CHK, or a biologically active fragment, analog, or derivative of CHK which is then expressed in the breast tissue.

As described herein, for the first time, Csk-homologous Kinase has been identified as playing an important role in signaling in neoplastic breast tissue and as functioning as a negative regulator of ErbB-2. As a result of this work, novel methods of detecting and inhibiting breast cancer are now available.

BRIEF DESCRIPTION OF THE DRAWINGS

FIG. 2A–B shows the nucleotide (SEQ ID NO: 1) and deduced amino acid sequence (SEQ ID NO: 2) of two overlapping matk CDNA clones representing the full-length cDNA. Nucleotide numbers are shown on the left. The putative initiation codon at nucleotide position 263 is shown in bold type.

FIG. 3 shows the nucleotide sequence (SEQ ID NO: 3) and deduced amino acid sequence ((SEQ ID NO: 4) of a CHK fragment. Specific primer positions are indicated.

DETAILED DESCRIPTION OF THE INVENTION

Figure 1A:
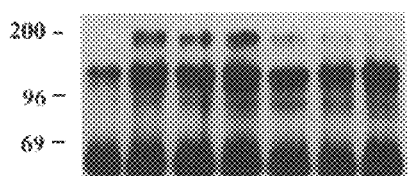
FIGS. 1A–D depict autoradiographs showing the association of the CHK-SH2 domain with ErbB-2 upon stimulation with HRG. Lysates were precipitated with the CHK-SH2 GST fusion protein and immunoblotted with monoclonal antiphosphotyrosine antibody (PY20), (A), or with polyclonal anti-ErbB-2 antibodies (B). Immunoprecipitations of the same lystates were performed using 3E8 monoclonal anti-ErbB-2 antibody and blotted with PY20 (C) or with anti-ErbB-2 antibodies (D). Molecular size markers are indicated on the left (kDa).

The family of protein tyrosine kinases (PTKs) includes oncogenes and growth factor receptors, several of which have been linked to the pathogenesis and progression of certain cancers (Bishop, J. M., *Genes. Dev.*, 9:1309–1315 (1995)Cancer, W. G., et al., *Breast Can. Res. & Treat.*, 35:105–1114 (1995) ). Increasing evidence indicates that the c-src proto-oncogene may play an important role in breast cancer. Human breast cancers often show much higher levels of src protein kinase activity than normal adjacent epithelium (Hennipman, A., et al., *Cancer Research*, 49:516–521 (1989), Ottenhoff-Kalff, A. E., et al., *Cancer Research*, 52:4773–4778 (1992) ). Indeed, about 70% of the elevated total tyrosine kinase activity found in primary breast cancers can be attributed to increased src activity. Involvement of pp60c-src with two major signaling pathways in human breast cancer has been demonstrated. In human breast carcinoma cell lines, the SH2 domain of src binds to activated epidermal growth factor (EGF-R) and $p_{185}^{ErbB-2}$, a receptor tyrosine kinase (Luttrell, D. K., et al., *Proc. Natl. Acad. Sci. USA*, 91:83–87 (1994) ).

Overexpression of the receptor tyrosine kinase ErbB-2 (also termed neu/HER-2) has been also associated with the development of breast cancer (Salmon, D. J., et al., *Science*, 244:707–712 (1989), Williams, T. M., et al., *Pathobiology*, 59:45–52 (1991) ). A common pathway linking the activation mechanisms in ErbB-2 amplification in breast cancer is increased tyrosine kinase activity which leads to cellular transformation (Olsson, H., et al., *J. Natl. Cancer. Inst.*, 83:1483–1487 (1991) ).

Four members of the ErbE (HER) family are presently know: $p_{170}^{ErbB-1}$ (epidermal growth factor receptor, EGR-R), $p185^{ErbB-2}$, $p180^{ErbB-3}$ and $p180^{ErbB-4}$. In particular, the overexpression of the $p185^{ErbB-2}$ correlates with a poor clinical prognosis in breast cancer (Beerli, R. R., et al., *Mol. Cell. Biol.*, 15:6496–6505 (1995), Holmes, W. E., et al., *Science*, 256:1205–1210 (1992), Wen, D., et al., *Cell*, 69:559–572 (1992) ). The overall amino acid homology within this receptor family ranges from 40–50%, and all the family members are characterized by two cysteine-rich regions in the extracellular domain, a single transmembrane region and a large cytoplasmic domain that exhibits tyrosine kinase activity (Wen, D., et al., *Cell*, 69:559–572 (1992) ).

Several ligands that bind to and stimulate the kinase activity of the ErbB family members have been identified and are classified as EGF-like ligands. EGF, HB-EGF, amphiregulin, betacellulin, epiregulin and transforming growth factor-α (TGF-α) are the ligands for the EGF-R (ErbB-1) (Cohen, B. D., et al., *J. Biol. Chem.*, 271:4813–4818 (1996),Johnson, G. R., et al.,*J. Biol. Chem.*, 268:2924–2931 (1993) ). Heregulin (HRG) and its rat homologue, neu differentiation factor (NDF), are a subfamily of neruegulins which are EGF-like ligands that bind to and activate both ErbB-3 and ErbB-4. Although none of these factors binds directly to the ErbB-2, both EGF and HRG induce its tyrosine phosphorylation, presumably by ligand-driven heterodimerization and cross-phosphorylation. Interestingly, ErbB-2, by heterodimerizing with the EGF-R and ErbB-3, confers high affinity binding sites for EGF and HRG, respectively (Beerli, R. R., et al., *Mol. Cell. Biol.*, 15:6469–6505 (1995), Marchionni, M. A., et al., *Nature*, 362:312–318 (1993) ).

Recently, a cytoplasmic tyrosine kinase, CHK (Csk Homologous Kinase), previously referred to as MATK (Megakaryocyte Associate Tyrosine Kinase), has been identified. The CHK protein, primarily expressed in hematopoietic cells and in human brain has an apparent molecular weight of 58 kD, and shares 50% homology with the human Csk (c-terminal src kinase). Like Csk, CHK contains SH3, SH2 and tyrosine kinase domains, and lacks the src family N-terminal myristylation and autophosphorylation sites. CHK was found to phosphorylate the inhibitory carboxyl-terminal conserved tyrosine of several src-related enzymes in vitro, including Lck, Fyn and c-src, and to reduce the elevated phosphotyrosine levels of src family kinases in Csk-deficient fibroblasts.

As described herein, for the first time, the interaction of CHK with ErbB-2 upon the activation of breast cancer cells by HRG has been demonstrated. This interaction occurred via the SH2 domain of CHK and was specific to the activated ErbB-2 receptor upon HRG stimulation. Also described herein for the first time, is the demonstration that CHK is expressed in human breast cancer cells but not in adjacent normal breast tissue cells.

The present invention relates to methods of detecting and treating breast cancer in mammals wherein the methods encompass the detection or use of CHK protein, or nucleic acids encoding CHK. As defined herein, the term CHK protein encompasses the full-length CHK protein as described in Bennett, B. D., et al., *J. Biol. Chem.*, 269::1068–10741 (1995), the teachings of which are hereby incorporated by reference, and also biologically active CHK fragments, derivatives analogs, variants and mutants.

The term "biologically active" CHK fragments, derivatives analogs, variants and mutants is defined herein as the activity encompassing the specific association of CHK with the intracellular domain of ErbB-2, or chimeric ErbB-2 molecules, such as EGF-ErbB-2 molecules. As described herein, this association is mediated by the SH2 domain of CHK. Association of CHK with ErbB-2 can be demonstrated, for example, using immunoprecipation experiments as described in the Examples. Because CHK is a tyrosine kinase, biological activity is also defined herein as the ability of CHK to phosphorylate tyrosine, specifically the phosphorylation of the carboxyl-terminal tyrosine of src-related kinases, thereby repressing their activity. Several src-related kinases include Lck, Fyn and c-src. Assays that demonstrate the phosphorylation ability of CHK include immune complex kinase reactions and the ability to phosphorylate kinases in yeast co-expression systems as described in (Avraham, S., et al., *J. Biol. Chem.*, 270:1833–1842 (1995), Chow, L. M., et al., *Oncogene*, 59:3371–3374 (1994), Klags, S., et al., *Proc. Natl. Acad. Sci. USA*, 19:2597–2601 (1994) and Davidson, D., et al., *J. Bil. Chem.*, 272:1355–1362 (1997) ), the teachings of which are hereby incorporated by reference. Other methods of measuring kinase activity are known to those of skill in the art.

Another biological activity of CHK is the antigenic property of inducing a specific immunological response as determined using well-known laboratory techniques. For example, a biologically active CHK can induce an immunological response which produces antibodies specific for CHK (anti-CHK antibodies).

To be "functionally" or "biologically active" a CHK protein fragment, analog, mutant or derivative typically shares substantial sequence (amino acid or nucleic acid) identity (e.g., at least about 65%, typically at least about 80% and most typically about 90–95%) with the corresponding sequences of endogenous, or naturally occurring, CHK and possesses one or more of the functions of endogenous CHK thereof. For example, a biologically active CHK fragment typically shares sequence homology with endogenous CHK protein in the domains, e.g., tyrosine kinase domain, or SH2 domain, important for biological activity.

CHK of the present invention is understood to specifically include CHK proteins having amino acid sequences analogous to the sequence of the endogenous CHK. Such proteins are defined herein as CHK analogs. An "analog" is defined herein to mean an amino acid sequence with sufficient identity to the amino acid sequence of endogenous CHK protein to possess the biological activity of the protein. For example, an analog of a polypeptide can be introduced with "silent" changes in the amino acid sequence wherein one or more amino acid residues differ form the amino acid sequence of CHK, yet possess e.g., kinase activity or associates with ErbB-2. Examples of such differences include additions, deletions or substitutions of residues. Also encompassed by the present invention are proteins that exhibit greater or lesser biological activity of CHK protein.

The present invention also encompasses biologically active fragments of CHK protein. Such fragments can include only a part of the full-length amino acid sequence of CHK yet possess iological activity. As used herein, a "biologically active fragment" means a fragment that can exert a biological or physical effect of the full-length protein, or has a biological characteristic, e.g., antigenicity, of the full-length protein. The antigenicity of a peptide fragment can be determined, for example, as described in Geysen, et al., WO 84/03564, the teachings of which are herein incorporated by reference. Such activities and characteristics are described above. Such fragments can be produced by amino and carboxyl terminal deletions as well as internal deletions. Also included are active fragments of the protein as obtained by enzymatic digestion. Such peptide fragments can be tested for biological activity as described herein. "Derivatives" and "variants" of CHK are CHK proteins that have been modified. They include CHK proteins that have been modified by alterations in their amino acid sequence. They also include truncated and hybrid forms of CHK. "Truncated" forms are shorter versions of CHK, typically modified so as to remove the C-terminal regions which effect binding or secretion. "Hybrid" or "chimeric" forms are CHK proteins that are composed of one or more CHK proteins combined with one or more other proteins, such as another kinase.

Variants can be produced using methods discussed below. The CHK gene can be mutated in vitro or in vivo using techniques well known to those of skill in the art, for example, site-specific mutagenesis and oligonucleotide mutagenesis. Manipulations of the CHK protein sequence can be made at the protein level as well. Any of numerous chemical modifications can be carried out by known techniques including, but not limited to, specific chemical cleavage by cyanogen bromide, trypsin and papain. It can also be structurally modified or denatured, for example, by heat or by being immobilized on a solid surface.

The amino acid sequences of the CHK proteins of the present invention can be altered to optimize CHK association with ErbB-2 by methods known in the art by introducing appropriate nucleotide changes into native or variant DNA encoding the CHK, or by in vitro synthesis of the desired CHK. Alterations can be created outside or within the CHK SH2 domain.

In general, mutations can be conservative or non-conservative amino acid substitutions, amino acid insertions or amino acid deletions. The mutations can be at or near (within 5 or 10 amino acids) the SH2 binding domain. More preferably, DNA encoding an CHK amino acid sequence variant is prepared by site-directed mutagenesis of DNA that encodes a variant or a nonvariant version of CHK. Site-directed (site-specific) mutagenesis allows the production of CHK variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed.

Typically, a primer of about 20 to 25 nucleotides in length is preferred, with about 5 to 10 residues on both sides of the junction of the sequence being altered. In general, the techniques of site-specific mutagenesis are well known in the art, as exemplified by publications such as Edelman et al., *DNA* 2, 183 (1983). The site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, A. Walton, ed., Elsevier, Amsterdam (1981). This and other phage vectors are commercially available and their use is well-known to those skilled in 15 the art. A versatile and efficient procedure for the construction of oligonucleotide directed site-specific mutations in DNA fragments using M13-derived vectors was published by Zoller, M. J. and Smith, M., *Nucleic Acids Res.* 10:6487–6500 (1982) ). Also, plasmid vectors that contain a single-stranded phage origin of replication can be employed to obtain single-stranded DNA. Veira et al., *Meth. Enzymol.* 153:3 (1987). Alternatively, nucleotide substitutions can be introduced by synthesizing the appropriate DNA fragment in vitro, and amplifying it by PCR procedures known in the art.

In general, site-specific mutagenesis can be performed by first obtaining a single-stranded vector that includes within its sequence a DNA sequence that encodes the relevant protein. An oligonucleotide primer bearing the 30 desired mutated sequence is prepared, generally synthetically, for example, by the method of Crea et al., *Proc. Natl. Acad. Sci. USA* 75, 5765 (1978). This primer can then be annealed with the single-stranded protein sequence-containing vector, and subjected to DNA-polymerizing enzymes such as *E. coli* polymerase I Klenow ragment, to complete the synthesis of the mutation-bearing strand. Thus, a heteroduplex is formed wherein one strand encodes the original non-mutated sequence and the second strand bears the desired mutation. This heteroduplex vector can then be used to transform appropriate host cells such as JM101 cells, and clones can be selected that include recombinant vectors bearing the mutated sequence arrangement. Thereafter, the mutated region can be removed and placed in an appropriate expression vector for protein production.

The PCR technique can also be used in creating amino acid sequence variants of an CHK. When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers can be designed to overlap the position of the mutation and to contain the mutation; the sequence of the other primer is preferably identical to a stretch of sequence of the opposite strand of the plasmid, but this sequence can be located anywhere along the plasmid DNA. It is preferred, however, that the sequence of the second primer is located within 500 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s) This product can be used to replace the corresponding region in the plasmid that served as PCR template using standard DNA technology. Mutations at separate positions can be introduced simultaneously by either using a mutant second primer or performing a second PCR with different mutant primers and ligating the two resulting PCR fragments simultaneously to the vector fragment in a three (or more) part ligation.

Another method for preparing variants, cassette mutagenesis, is based on the technique described by Wells et al. *Gene* 34, 315 (1985). The starting material can be the plasmid (or vector) comprising the CHK DNA to be mutated. The codon(s) within the CHK to be mutated are identified. There must be unique restriction endonuclease sites on each side of the identified mutation site(s). If such restriction sites do not exist, they can be generated using the above-described oligonucleotide-mediated mutagenesis method to introduce them at appropriate locations in the CHK DNA. After the restriction sites have been introduced into the plasmid, the plasmid is cut at these sites to linearize it. A double stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated CHK DNA sequence, that can be expressed to produce CHK with altered binding activity.

Specifically encompassed by the present invention are methods of detecting the presence or absence of CHK protein in mammalian cells wherein detection of the presence of (e.g., the expression of) CHK is indicative of breast cancer. A biological sample to be tested for the presence or absence of CHK protein is obtained from the mammal. Typically, the sample is breast tissue or tissue adjacent to the breast. The tissue sample can include lymph nodes. The sample is typically obtained by biopsy techniques well known to those of skill in the art.

CHK protein expression can be detected in a tissue sample by immunohistochemical techniques as described herein. For example, the tissue can be imbedded in paraffin or frozen and sectioned in to thin slices, typically mounted on microscope slides. The tissue is contacted with an anti-CHK antibody under conditions suitable for the anti-CHK antibody to specifically bind to CHK present in the tissue sample as described herein. The anti-CHK antibodies can be monoclonal or polyclonal. The antibody can be detectably labeled, for example, with a florescent dye. Alternatively, a second antibody that is detectably labeled can be used. For example, if the first antibody is a mouse anti-CHK antibody, a second antibody can be detectably labeled rabbit anti-mouse. Techniques for producing, purifying and labeling antibodies are well-known to those of skill in the art.

Expression of CHK protein can also be detected by Western blot (immunoblot) analysis using anti-CHK antibodies as described herein. Additionally, the expression of CHK protein can be detected by immunoprecipitation using anti-CHK antibodies, also as described herein. Additional techniques suitable for use to detect the presence of CHK protein includes e.g., immunofluorescence staining, confocal staining and ELISA when using soluble lysates. Such techniques are also well known to those of skill in the art.

Detection of the presence or absence of CHK can also be accomplished by the detection of the presence or absence of nucleic acids, either DNA or RNA, encoding the CHK protein in a biological sample. The biological sample, e.g., breast tissue, can be prepared in a manner that renders the nucleic acid encoding CHK available for hybridization with a nucleic acid probe that specifically hybridizes with a nucleic acid sequence that encodes all, or a portion, of CHK. For example, Northern blot analysis, or Southern blot analysis can be used to detect the presence of CHK RNA or DNA in a biological sample. These techniques are well-known to those of skill in the art. (See e.g., Sambrook et al. *MOLECULAR CLONING: A LABORATORY MANUAL,* Cold Spring Harbor Laboratory Press, Cold Spring Harbor, N.Y., (1989) or Ausubel et al., *CURRENT PROTOCOLS IN MOLECULAR BIOLOGY,* J. Wiley and Sons, New York, N.Y. (1992) ). For example, the standard Southern blot methods includes extracting genomic DNA from the sample, and digesting the genomic DNA with suitable restriction enzymes to obtain DNA fragments. The DNA fragments are then separated by electrophoretic means on e.g., agarose gels and transferred to nylon membranes which are exposed to detectably-labeled probes under conditions sufficient for the probes to specifically hybridize to nucleic acids encoding CHK. Detection can be accomplished by, e.g., autoradiography, spectrometry or fluorometry.

Nucleic acid probes useful in the present invention comprise at least about 15 nucleotides, typically about 21 to 45 nucleotides and most typically about 100 nucleotides. This number of nucleotides typically provides the minimal length required of a probe that would specifically hybridize to a CHK-encoding sequence. The probes are of a specificity and sufficient length to form stable hybrid duplexes with the target sequence under stringent conditions. As used herein, stringent conditions are defined as conditions under which specific hybrid duplexes will be stable and maintained and under which non-specific hybrid duplexes will be not be stable (e.g., stable during wash conditions while non-specific hybrid duplexes will be (eluted during wash conditions). Probes and conditions useful in the present invention are described in WO 5 93/15201, entitled "Novel Protein Tyrosine Kinases", the teachings of which are herein incorporated in their entirety by reference (Also see FIG. 3, SEQ ID NO: 3, which is a nucleic acid sequence encoding a CHK peptide). Techniques for identifying probes and conditions of stringency (e.g., moderate or high) are also well-known to those of skill in the art and e.g., are described in Sambrook et al. *MOLECULAR CLONING: A LABORATORY MANUAL,* Cold Spring Harbor Laboratory Press, Cold Spring Harbor, N.Y., (1989) or Ausubel et al., *CURRENT PROTOCOLS IN MOLECULAR BIOLOGY,* J. Wiley and Sons, New York, N.Y. (1992).

It is important to note that the nucleotide sequences of probes that are useful in the present invention need not be fully complementary to the target sequence. Probes need only be substantially complementary. As defined herein, substantially complementary means that the probe sequence is sufficiently similar in sequence identity to the target sequence that the probe specifically hybridizes with the target sequence under specified conditions. For example, non-complementary bases can be interspersed within the probe sequence, or the probe can be longer or shorter than the target sequence, provided that the probe still specifically hybridizes with the target sequence.

Detection of hybrid duplexes is typically accomplished by the use of detectably labeled probes. Such labels and methods of labeling probes are well-known to those of skill in the art. For example, labels can be radiolabels, chemiluminescent labels, fluorescent labels, biotin, enzymes or other labels known to those of skill in the art. Alternatively, the probe can be unlabeled but detectable by subsequent binding or hybridization to a second, detectably labeled molecule.

Detection of nucleic acids encoding CHK can also be accomplished by amplification techniques which directly amplify the target nucleic acid present in a sample, for example, by polymerase chain reaction (PCR) (See e.g., Saiki, et al., *Science,* 230:1350–1353 (1986) or ligase chain reaction (LCR) (See e.g., Weiss, R., *Science,* 254:1292–1293 (1991) ). Such amplification techniques can also be used a preliminary steps for detection techniques described above. For example, conditions and specific primers suitable for use in a PCR method to amplify nucleic acids encoding CHK are described herein.

In situ hybridization analysis on tissue samples can also be used to detect the presence or absence of CHK in a biological sample. Such techniques are also well-known to those of skill in the art. (See for example, Sure Site II System™ hybridization kit by NoVagen.)

The present invention also encompasses the use of the CHK proteins and nucleic acids encoding these proteins as a basis of rational drug design to produce biologically active CHK analogs that have substantially comparable, or lesser or greater biological activity of CHK. Also encompassed are the use of the CHK proteins to identify small molecules which interact with CHK and, thus, can act as agonists, antagonists or inhibitors of CHK activity.

A further embodiment encompassed by the present invention includes methods of inhibiting neoplastic (tumor) cell growth by supplying CHK to cells. Specifically encompassed by the present invention are methods that inhibit ErbB-2 mediated-breast cancer cell growth. Cells that are in need of CHK and are supplied with, or receive CHK protein, are referred to herein as target or recipient cells. The recipient cells are either substantially deficient in CHK (e.g., fail to produce an amount of CHK sufficient to suppress neoplastic growth, or hyperplasia, which is abnormal growth) or produce adequate amounts of CHK, but the CHK produced is functionally abnormal (e.g., the CHK lacks biological activity to suppress neoplastic growth). As defined herein, the term "inhibit" means either to completely suppress or prevent neoplastic cell growth or to substantially, or significantly decrease neoplastic or hypeplastic cell growth. Inhibition or decrease of cancer cell growth, or hyperplasia, can be measured as described herein, e.g., by comparing growth of breast tumor cells that have been supplied with CHK to breast tumor cells that have not been supplied with CHK, and by other methods well-known to those of skill in the art.

CHK protein, peptide or a biologically active fragment thereof, or a CHK analog or derivative, can be supplied to mammalian breast tissue that manifests neoplastic cell growth, or is at risk of producing neoplastic cell growth e.g., hyperplastic tissue. CHK can be supplied to (e.g., introduced into) the target recipient cells by methods well-known to those of skill in the art. For example, CHK can be introduced into recipient cells by injection of a pharmaceutical composition that contains an effective amount of CHK in a physiologically compatible solution, or by a liposome preparation that contains an effective amount of CHK. Specifically encompassed by this invention is the topical application of liposomes in a cream or ointment which contain an effective amount of CHK. An effective amount of CHK is defined herein as an amount of CHK which inhibits neoplastic or hyperplastic cell growth, specifically ErbB-2 mediated breast cancer cell growth.

Suitable physiologically acceptable carriers include but are not limited to water, salt solutions, alcohols, gum arabic, vegetable oil, benzyl alcohols, polyethylene glycols, gelatine, carbohydrates such as lactose, amylose or starch, magnesium stearate, talc, silicic acid. Viscous paraffin, perfume oil, fatty acid esters, hydroxymethylcellulose, polyvinyl pyrrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers and the like which do not deleteriously react with the active compounds. They can also be combined, where desired, with other active agents, e.g., enzyme inhibitors, to further reduce metabolic degradation.

For topical application, there are employed as nonsprayable forms, viscous semi-solid or solid forms comprising a carrier compatible with topical application and having a dynamic viscosity preferably greater than water. Suitable formulations include but are not limited to solutions, suspensions, emulsions, creams, foams, ointments, powders, liniments, salves, aerosols, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air. Also included are transdermal patches as discussed, for example, in Wo 93/07870, the teachings of which are incorporated by reference.

Alternatively, CHK can be supplied to the recipient cells by introducing a nucleic acid sequence encoding CHK, or a biologically active fragment, analog, or derivative of CHK which is then expressed in the recipient cells. Methods of introducing nucleic acids encoding specific proteins such as CHk are well-known to those of skill in the art. For example, expression vectors can be designed and produced that contain a nucleic acid insert which encodes CHK or a biologically active fragment of CHK. Methods to construct these expression vectors are well-known to those of skill in the art. For example, described herein is an expression vector comprising vaccinia virus useful for expressing a DNA insert encoding CHK. In addition to vaccinia virus, other virus or plasmid vectors, such as retroviruses, or plasmid vectors can be used to introduce nucleic acids encoding CHK into recipient cells. Additionally naked DNA can be injected into recipient cells, or methods such as elctroporation, co-precipitation or a "gene gun" can be used to deliver the DNA to the recipient cells.

Other techniques using naked plasmids or DNA, and cloned genes encapsidated in targets liposomes or in erythrocyte ghosts, can be used to introduce the receptor into the host (Friedman, T., *Science,* 244:1275–1281 (1990); Rabinovich, N. R., et al., *Science,* 265:1401–1404 (1994) ). The construction of expression vectors and the transfer of vectors and nucleic acids into various host cells can be accomplished using genetic engineering techniques, or by using commercially available kits as described in Sambrook, J., et al. *Molec. Cloning,* Cold Spring Harbor Press (1989) or Ausubel, F. M., et al. *Current Protocols in Molecular Biology,* Greene Publishing Assoc. and Wiley-Interscience (1989) the teachings of which are hereby incorporated, in their entirety, by reference.

Cells from a patient's tumor can be analyzed by the diagnostic methods described above to determine the presence of CHK or to determine the biological activity of CHK present in their cells. A vector as described herein, containing a nucleic acid encoding CHK and operably linked to expression control elements required for the expression of a protein in the recipient cells, is then introduced into the patient, either at the site of the tumor or by intravenous or other parenteral injection in order to reach any tumor cells that may have metastasized to other sites. The introduction may be repeated as necessary in order to achieve the desired effect of inhibiting neoplastic growth. A description of techniques that may be used to specifically target breast cells is described in EP 0 699 754 A1, the teachings of which are herein incorporated by reference.

Thus, as a result of the work described herein, novel methods of detecting and inhibiting breast cancer, or hyperplastic growth that may result in cancer, are now available.

The following examples more specifically illustrate the invention and are not intended to be limiting in any way.

EXAMPLE 1: EXPRESSION OF CHK IN HUMAN BREAST CANCER TISSUE

Materials

Recombinant heregulin (rHRG(1, 177–244), rabbit polyclonal anti-ErbB-2 antibodies, and 3E8-monoclonal anti-ErbB-2 antibodies, were obtained from Genentech, Inc. (San Francisco, Calif.), Levi, A. D., Bunge, R. P., Lofgren, J. A., Meima, L., Hefti, F., Nikolics, K., and Sliwkowski, M. X., *J. Neurosci.,* 15, 1329–1340 (1995) ). EGF and IL-6 were purchased from Collaborative Biomedical Products (Bedford, Mass.) and from R & D Systems (Minneapolis, Minn.) respectively. Monoclonal anti-phosphotyrosine antibody (PY20) conjugated to horse radish peroxidase (HRP) was obtained from Zymed, Inc. (San Francisco, Calif.). Polyclonal antibodies for EGF-R, ErbB-3, ErbB-4 and polyclonal anti-CHK (anti-LSK) antibodies were obtained from Santa Cruz Biotechnology (Santa Cruz, Calif.). Anti-GST monoclonal antibodies were purchased from Pharmacia Biotech, Inc. (Piscataway, N.J.). GST fusion proteins containing the NH2-SH2 domain of p85 PI3 kinase and SH2-SH2-SH3 domains of PLC-1 were obtained from Santa Cruz Biotechnology. The primers for the polymerase chain reaction (PCR) were synthesized by an automated DNA Synthesizer (Applied Biosystems, Model 394). Reagents for electrophoresis were obtained from BioRad (Hercules, Calif.). ECL reagents were purchased from Amersham Corp. (Arlington Heights, Ill.). All other reagents were purchased from Sigma (St. Louis, Mo.).

Experimental Procedures

Immunohistochemical staining was performed on paraffin-embedded 5 mm-thick tissue sections of human breast cancer. Sections were deparaffinized in xylene and then incubated in decreasing concentrations of ethyl alcohol. After several rinses in water, the slides were incubated in methanol/hydrogen peroxide (1:4), briefly rinsed in water and then in PBS (pH 7.6). Subsequent immunohistochemical staining was performed using a 1:100 dilution in PBS of rabbit anti-CHK antisera (1 hr incubation) followed by the addition of the secondary antibodies, peroxidase-conjugated rabbit anti-mouse IgG (Sigma) at 50 µg/ml in PBS.

Analyses of CHK expression in human breast cancer tissues at different stages were performed using immunohistochemistry on paraffin sections. Results (Table 1) revealed that CHK is expressed in the majority of breast cancers, but was not detected in normal adjacent tissue.

TABLE 1

CHK Expression in Primary Breast Cancer Tissues

| BREAST CANCER PATIENTS | NO. PATIENTS (+) FOR CHK |
| --- | --- |
| Stage I | 32/41 |
| Stage II | 29/35 |
| Stage III | 4/4 |
| Unknown Stage | 5/6 |
| Normal Breast | 0/3 |
| Fibroadenoma | 0/6 |

Immunohistochemical staining was performed on paraffin embedded sections of infiltrating ductal carcinoma using anti-CHK antibodies.

EXAMPLE 2: CHK IS ASSOCIATED WITH ACTIVATED ErbB-2 UPON STIMULATION WITH HRG

Figure 1C:
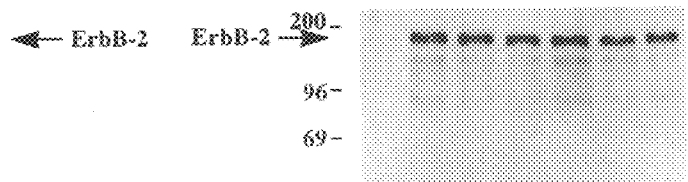
Figure 1B:
Figure 1D:

Experiments were performed using the T47D breast cancer cell line and the GST-fusion protein containing the SH2 domain of CHK (CHK-SH2). T47D cells express the ErbB family receptors and the CHK protein as observed by a immunohistochemistry. The T47D human breast cancer cell line was obtained from ATCC (American Type Culture Collection, Rockville, Md.). T47D cells were grown in RPMI-1640 medium (GIBCO/BRL, Life Technologies, Gaithersburg, Md.) supplemented with 10% fetal bovine serum (FBS) and 3–5 (g/ml insulin (Sigma). Prior to stimulation with HRG, cells were starved overnight in media containing lo FBS and then for 4 hr in serum-free medium. The starved cells were then stimulated with HRG (10 nM) for the indicated time points (FIGS. 1A–D). Cells were lysed, and the supernatants were incubated with the purified CHK-SH2 fusion protein (FIGS. 1A, 1B) or with the 3E8 monoclonal antibody to ErbB-2 (FIGS. 1C, 1D). The co-precipitated proteins were analyzed on 7% SDS-PAGE, and immunoblotted with PY20 (FIGS. 1A, 1C).

As shown in FIG. 1A, a tyrosine-phosphorylated 185 kD protein was associated with CHK-SH2 within 2 min of the HRG stimulation. The association of the 185 KD with CHK-SH2 was maximal at 2–8 min after HRG stimulation and then gradually decreased. In order to determine whether the 185 kD protein was ErbB-2, the blot was deprobed and reblotted with polyclonal anti-ErbB-2 antibody. As shown in FIG. 1B, the 185 kD protein was confirmed to be the ErbB-2 protein. These results indicated that the CHK protein can interact with the HRG-activated ErbB-2 receptor.

When lysates from HRG-treated cells were immunoprecipitated with the 3E8 monoclonal anti-ErbB-2 antibody, the pattern of the phosphorylated ErbB-2 was different from that of the ErbB-2 precipitated with the SH2 domain of CHK (compare FIG. 1C with FIG. 1A). Blotting of the same samples with the polyclonal anti-ErbB-2 antibody (FIG. 1D) confirmed these observations.

CHK-SH2 fusion proteins also precipitated other as of yet unidentified tyrosine-phosphorylated proteins as shown in FIG. 1A. However, these phosphorylated proteins were also precipitated from the unstimulated cells and their phosphorylation pattern did not appear to change over the time course of these studies.

EXAMPLE 3: THE ASSOCIATION OF CHK WITH ErbB-2 IS SPECIFIC FOR HRG STIMULATION

In order to determine whether the observed association of CHK with ErbB-2 was receptor-specific and stimulus-specific, experiments were performed to analyze whether CHK could associate with either the EGF-R or IL-6 receptors which are both known to be expressed in T47D cells. The association of CHK-SH2 with ErbB-2 in lysates from HRG, EGF and IL-6 stimulated cells was compared. T47D cells were serum starved as described above and then activated either with HRG (10 (nM) for 8 min or with (EGF (100 ng/ml) or IL-6 (100 ng/ml) for 5 min. The experimental time points and the concentrations of EGF and IL-6 were optimized in initial kinetic studies. The stimulated cells were lysed and precipitated with the CHK-SH2 fusion protein as described above. The precipitates were then analyzed on SDS-PAGE and immunoblotted with PY20 antibodies or with polyclonal anti-ErbB-2 antibodies. Only HRG stimulation induced the association of ErbB-2 with the purified CHK-SH2 fusion protein. EGF or IL-6 stimulation failed to induce CHK-SH2 association either to ErbB-2, or to the EGF-receptor or the IL-6 receptor.

The association of ErbB-2 with other SH2 domain-containing signaling molecules such as p85 of PI3-kinase, PLC-1 or Shc was also examined. The SH2-SH2-SH3 domain of PLC-1 was found to be associated with the HRG-activated ErbB-2 as well as with Shc. The SH2 domain of PI3-kinase precipitated ErbB-2, probably as a result of the ErbB-2 heterodimerization with ErbB-3. Taken together, these results indicate that ErbB-2 associates with all three signaling molecules in HRG-activated T47D cells.

Experiments were also performed to show that the SH3 domain of CHK is not involved in the interaction between CHK and ErbB-2.

The potential involvement of other domains of CHK in the interaction with ErbB-2 was also examined. GST-fusion proteins containing the SH3 domain of CHK (CHK-SH3), the N-terminal domain plus SH3 domain (NH2-SH3), the SH3 and SH2 domains of CHK (SH3-SH2), the SH2 domain of CHK as well as the GST protein alone were prepared as follows.

Generation of Flag-CHK construct in pCDNA3 vector:

The CHK cDNA (1.6 kb, (SEQ ID NO: 1) was cloned into EcoRI sites in the pCDNA3 neo vector. The nucleotide sequence for the Flag epitope (Asp-Tyr-Lys-Asp-Asp-Asp-Asp-Lys) (SEQ ID NO: 5) was introduced to the 5' end of the ORF (open reading frame) of the CHK cDNA sequence by PCR, using 1.6 kb CHK cDNA as a template. The 5' sense primer included a BamH I restriction site, ATG initiation codon, the Flag sequence and CHK sequences from nucleotides #269 to #295 of SEQ ID NO: 1, FIG. 2 (Bennett, B. D., et al. (1994) *J. Biol. Chem.* 269, 1068–1074), the teachings of which are herein incorporated, in their entirety, by reference). The 3'-antisense primer was composed of CHK sequences from nucleotides #510 to #481 of SEQ ID NO: 1. The PCR product was double digested with BamHI and BstEII (New England Bio Labs, Beverly, Mass.), gel-purified and then cloned into BamHI, and BstEII sites in the pDNA3 neo-Flag-CHK. The construct was analyzed by restriction mapping and nucleotide sequencing.

Transfection:

Transfection of MCF-7 cells was performed using the LipofectamineTM (Gibco/BRL) according to the manufacturer's protocol. The transfected cells were selected in 1.2 mg/ml G418 (Sigma). Positive transfectants were chosen based on their immunoreactivity on Western blots probed with polyclonal anti-CHK and monoclonal anti-Flag (M5) antibodies (Eastman Kodak Company, New Haven, Conn.).

Construction and purification of GST-fusion proteins of CHK:

To express the NH2-SH3 and SH3-SH2 domains of CHK as GST-fusion proteins, the corresponding DNA sequences were amplified by PCR with sense and antisense primers of CHK cDNA which contained BamHI and EcoRI restriction sites. For the NH2-SH3 construct, we used the sense primer from nucleotides #4 to #27 SEQ ID NO: 1 and the antisense primer from nucleotides #343 to #321 of SEQ ID NO: 1. For the SH3-SH2 construct, we the sequence from nucleotides #127 to #150 of SEQ ID NO: 1 was used as the sense primer and from nucleotides #657 to #634 SEQ ID NO: 1 as the antisense primer. The DNA fragments obtained from PCR were restriction digested with BamHI and EcoRI and ligated into the pGEX-2T vector (Pharmacia). The sequence and orientation were confirmed by sequencing both strands. Construction of the GST-fusion proteins of CHK-SH2 and CHK-SH3 were performed as described in Jhun, B. H., Rivnay, B., Price, D., and Avraham, H. (1995) J. Biol. Chem. 270, 9661-9666.

GST-fusion proteins were produced by the induction of transformed bacteria using 10 mM isopropyl-(-thiogalactopyranoside (IPTG), and purified on a large scale by affinity chromatography on glutathione-sepharose beads (Pharmacia) according to the manufacturer's protocol.

HRG-stimulated T47D cell lysates were incubated with the different GST-fusion proteins, analyzed by SDS-PAGE, and immunoblotted either with PY20, rabbit anti-ErbB-2 antibody or with anti-GST antibody. Neither the SH3 domain of the CHK protein nor the NH2-SH3 domain precipitated ErbB-2. Binding to ErbB-2 was detected only in the presence of the CHK-SH2 and CHK-SH3-SH2 fusion proteins. As expected, no binding was detected when the same lysates were incubated with the GST protein alone. The amounts of the different fusion proteins loaded on the gel were comparable. These results confirm that CHK can interact with the HRG-stimulated ErbB-2 in a specific manner via its SH2 domain.

EXAMPLE 4: IN VIVO ASSOCIATION OF INTACT CHK WITH ErbB-2

The MCF-7 human breast cancer cell line was obtained from. ATCC (American Type Culture Collection, Rockville, MD). The MCF-7 cells were grown in MEM (GIBCO) supplemented with 10% FBS, 5 µg/ml insulin (Sigma), 1 mM non-essential amino acids and 1 mM sodium pyruvate. Prior to stimulation, cells were starved overnight in media containing 1% FBS and then for 4 hr in serum-free medium.

To further confirm the association of ErbB-2 with CHK, the CHK protein was overexpressed in MCF-7 breast cancer cells. CHK expression in MCF-7 cells was detected only by PCR analysis. Expression of the ErbB receptor family in MCF-7 cells was similar to that observed in T47D cells. Stable transfections were performed using the Flag-CHK pCDNA3 neo construct as described above. The transfected cells were analyzed for CHK expression by Western blot using anti-Flag and anti-CHK antibodies and also by immunofluorescence using confocal microscopy. MCF-7 cells transfected with Flag-CHK pCDNA3 neo (Flag-CHK), MCF-7 cells transfected with the pCDNA3 neo vector alone, or untransfected MCF-7 control cells, were stimulated with HRG and then lysed.

Immunoprecipitation studies were performed as follows. Approximately $5 \times 10^6$ cells/plate were starved overnight in media containing 1% FBS, followed by additional starvation in serum-free medium for 4 hr at 37° C. The starved cells were then stimulated with 10 nM HRG for 8 min or with 100 ng/ml EGF or 100 ng/ml IL-6 for 5 min at room temperature. The stimulation was terminated by the addition of an ice-cold lysis buffer (0.1% SDS, 1% Triton X-100, in Tris-buffered saline containing 10% glycerol, 1 mM EDTA, 0.5 mM Na3VO4, 0.2 mM phenylmethylsulfonyl fluoride, 1 µg/ml aprotinin, and 10 mM leupeptin). Lysates were pre-cleared by centrifugation (14,000 rpm, 15 min) and then incubated for 90 min at 4° C. with 10 µg of GST-fusion proteins coupled to glutathione-sepharose beads. The beads were washed three times with the lysis buffer. For the immunoprecipitation experiments, polyclonal anti-CHK antibody, monoclonal anti-ErbB-2 antibody, 3E8 (10 µg/ml), polyclonal anti-ErbB-3 antibody (10 µg/ml) or polyclonal anti-ErbB-4 antibody (10 µg/ml) were used. SDS-sample buffer was added to the samples and analyzed on 7% polyacrylamide SDS-PAGE. Proteins were transferred onto nitrocellulose or Immobilon-PTM (Millipore, Inc., Bedford, Mass.) membranes. Bound proteins were immunoblotted with anti-phosphotyrosine antibody (PY20), polyclonal anti-ErbB-2 antibody, or polyclonal anti-CHK, EGF-R, ErbB-3 or ErbB-4 antibodies. The blots were developed using the enhanced chemiluminescence (ECL) system (Amersham). Blots were stripped for 30 min at 550C in stripping buffer (100 mM 2-mercaptoethanol, 2% SDS, 62.5 mM Tris-HCl, pH 6.7), according to the manufacturer's protocol (Amersham).

The 185 KD tyrosine-phosphorylated protein was immunoprecipitated with anti-Flag antibodies or anti-CHK antibodies only in HRG-stimulated Flag-CHK transfected cell lysates, but not in the untransfected MCF-7 cell lysates or the MCF-7 cell lysates transfected with the pcDNA3-neo Flag vector alone. Blotting with the anti-ErbB-2 antibody confirmed that the co-precipitated 185 KD protein was indeed the ErbB-2. Analysis of the total lysates from the same experiment revealed that the ErbB-2 was tyrosine-phosphorylated as a result of the HRG stimulation in the Flag-CHK cells as well as in the MCF-7 untransfected cells. The expression of ErbB-2 appeared to be equal in both the Flag-CHK and MCF-7 cells. Taken together, these in vitro and in vivo data indicate that the HRG-stimulated ErbB-2 associates with CHK through the SH2 domain.

EXAMPLE 5: INVOLVEMENT OF OTHER ErbB-2 FAMILY MEMBERS IN THE INTERACTION WITH CHK

To further investigate the possible involvement of other members of the ErbB family in the observed interaction between CHK and ErbB-2, co-immunoprecipitation experiments using MCF-7 cells transfected with Flag-CHK were performed. Flag-CHK transfected cells were stimulated with HRG, and then lysed and immunoprecipitated with anti-CHK antibody as described above. The immunocomplexes were separated by SDS-PAGE and immunoblotted with anti-ErbB-2 antibody or with anti-ErbB-3 antibody. The results indicated that anti-CHK antibody immunoprecipitated the HRG-activated ErbB-2. In contrast, no detectable ErbB-3 was found. However, the possibility that very low amounts of ErbB-3 were present in the precipitates as a result of the heterodimerization with the ErbB-2 receptor upon HRG stimulation cannot be excluded.

It was also investigated whether ErbB-4 interacted with CHK under these conditions, however, findings indicated that ErbB-4 was not involved in the ErbB-2-CHK association.

In order to confirm the presence and phosphorylation of the ErbB-3 as well as the heterodimerization of ErbB-3 with ErbB-2 in the Flag-CHK transfected cells, lysates from HRG-stimulated Flag-CHK cells were immunoprecipitated with anti-ErbB-3 antibodies or with anti-ErbB-2 antibodies. Both ErbB-3 and ErbB-2 were tyrosine-phosphorylated upon HRG stimulation and the formation of ErbB-2-ErbB-3 heterodimers was demonstrated by the presence of ErbB-2 in the precipitates of the anti-ErbB-3 antibodies. However, under these conditions, ErbB-3 was not detected in the samples immunoprecipitated with anti-ErbB-2 antibody. Taken together, these observations indicate that upon HRG stimulation, heterodimerization of ErbB-3 with ErbB-2 receptors occurred in the transfected cells, suggesting that the ErbB signaling in these cells is not altered.

To determine whether EGF-R (ErbB-1) might be involved in ErbB-2-CHK interactions, Flag-CHK MCF-7 transfected cells were serum-starved and then stimulated with HRG (10 nM) or with EGF (100 ng/ml). The lysates were immunoprecipitated with anti-CHK antibodies and analyzed by SDS-PAGE. Only the tyrosine-phosphorylated ErbB-2 protein was immunoprecipitated with anti-CHK-antibodies in the HRG-stimulated lysates. No tyrosine-phosphorylated proteins were detected in the immunoprecipitates with anti-CHK antibodies from the EGF-stimulated cells. Reprobing of this blot with anti-ErbB-2 or with anti-EGF-R antibodies confirmed that neither of these receptors were present in the CHK immunoprecipitates.

As a control, immunoprecipitations with anti-EGF-R antibodies of the EGF-stimulated Flag-CHK cell lysates as well as of lysates from untransfected MCF-7 cells were performed. The EGF-R and the ErbB-2 proteins were present in the immunoprecipitates from the EGF-stimulated cells as a result of the EGF-ErbB-2 heterodimerization. Probing of the same blot with anti-ErbB-2 or anti-EGF-R antibodies confirm this observation.

These analyses indicate that CHK associates via its SH2 domain with HRG- stimulated ErbB-2. This association is specific to HRG-stimulated ErbB-2 and does not appear to prominently involve other ErbB family members.

EXAMPLE 6: FUNCTIONAL ASSOCIATION OF CHK TO THE NEC(Val$^{664}$) AND TEC (GlU$^{664}$) EGF-ErbB-2 HYBRID RECEPTORS

ErbB-2 functions as a co-receptor for growth-regulatory molecules, including neuregulins. Replacement of the extracellular domain of ErbB-2 by the ligand biding domain of the receptor for EGF allows heterologous stimulation of the ErbB-2, which has been successfully exploited in signal transduction studies (Ben-Levy, R., et al., *EMBO J.*, 13;3302–3311 (1994). The transforming protein of ErbB-2, which contains a Glutamine residue (Glu$^{664}$) instead of a Valine (VAL$^{664}$) residue, is a constitutively active receptor permanently coupled to signaling pathways. To confirm that the association of CHK with ErbB-2 is mediated by the intracellular domain of ErbB-2 and not by other members of the ErbB-2 family, chimeric proteins that include the extracellular domain of the EGF receptor and the transmembrane and cytoplasmic domains of the ErbB-2, termed NEC (Val$^{664}$), or the point-mutated cytoplasmic domain of ErbB-2 (Glu$^{664}$) termed TEC, (kindly obtained from Dr. Y. Yarden (Department of Chemical Immunology, the Weizmann Institute of Science, Rehovot, Israel); Peles, E., et al., *J. Biol. Chem.*, 267:12266–12274 (1992) ) were used in this study. It is important to note that ErbB-2 does not directly bind to any of the EGF-like ligands. However, EGF and HRG induce the tyrosine phosphorylation of ErbB-2, presumably by ligand-driven heterodimerization and transphosphorylation. NIH3T3 cells were stably transfected with the chimeric plasmid EGF-TEC-ErbB-2 or with the chimeric plasmid EGF-NEC-ErbB-2. TEC and NEC cells (4×10$^6$ cells/plate) were serum-starved and then unstimulated or stimulated with 100 ng EGF at room temperature for 5 minutes. The lysates were divided to two parts: one half of the lysates were precipitated with the CHK-SH2 GST-fusion protein (l0ag) for 90 minutes at 4° C. (A-15 II, B-II). After washing, the precipitates were separated by 7% SDS-PAGE and immunoblotted with monoclonal anti-phosphotyrosine antibody (PY20), or with polyclonal anti-EGF-R antibodies. The other half of the lysates was immunoprecipitated using monoclonal antibodies for EGF-R for 16 h at 4° C. The washed precipitates were run on 7% SDS-PAGE and blotted with PY20 or with anti-EGF-R antibodies.

CHK association with both EGF-stimulated and unstimulated NEC and TEC was analyzed. Upon EGF Stimulation, CHK was found to associate via its SH2 domain with NEC, while its association with TEC was constitutive and not dependent on EGF stimulation. These results indicate that the CHK-SH2 domain specifically associates with the intracellular domain of ErbB-2.

EXAMPLE 7: GENERATION AND CHARACTERIZATION OF MCF-7 CELLS STABLY TRANSFECTED WITH CHK cDNA

In order to study the biological function(s) of CHK in human mammary epithelial cells, two known breast cancer cell lines, MCF-7 and T47D were chosen. Both cell lines, obtained from American Type Culture (ATCC, Rockville, Md.), are well established in the field of breast cancer research and used extensively as models (Gras-Porta, D., et al., *Mol. Cell. Biol.*, 15:1182–1191 (1995) Azijsen, R. M., et al., *Mol. & Cell Biol.*, 16:2554–2560 (1996) ). The expression of CHK in both these cell lines was analyzed. While T47D cells expressed CHK mRNA and protein as detected by Northern and Western blot analyses respectively, CHK expression in MCF-7 cells was detected only by PCR without evidence for significant levels of protein using immunoprecipitation or Western blotting. MCF-7 cells stably transfected with CHK cDNA that expressed CHK mRNA and CHK protein were generated. The MCF10-A cell line was used as a model for normal breast epithelial cells (Soule, H. D., et al., *Cancer Research*, 50:6075–6086 (1990). These cells lacked expression of CHK, as evaluated by Northern blot, PCR and Western blot.

Stable transfections of MCF-7 cells were performed using the FLAG-CHK-pcDNA3neo construct or the pcDNA3neo vector as a control. CHK protein can be detected either by CHK specific antibodies or FLAG monoclonal antibodies. The proliferation rate of MCF-7 cells transfected with the FLAG-CHK-pcDNA3neo construct overexpressing CHK protein was significantly reduced (p<0.001) compared to the untreated MCF-7 cells or to the MCF-7 cells transfected with the FLAG pcDNA3neo vector alone.

Confocal microscopy studies in these MCF-7 cells stably transfected with the FLAG-CHK-pcDNA3neo construct demonstrated that CHK was localized in the cytosol fraction. However, upon heregulin stimulation, CHK was translocated to the membrane. Taken together, these results, with the data on CHK-SH2 associating with ErbB-2, suggest that CHK is translocated from the cytosol to the membrane and associates with the ErbB-2 receptor upon ligand stimulation.

EXAMPLE 8: TUMOR DEVELOPMENT IN NUDE MICE

Initial studies have shown that CHK negatively regulates src activity and associates with ErbB-2 upon heregulin stimulation. Therefore, CHK might function as a negative regulator and might act to inhibit mitogenic signaling by c-src and ErbB-2. Interestingly, the proliferation rate of the MCF-7/CHK clone was reduced compared to the control MCF-7/neo clone or untransfected MCF-7 cells. Therefore, to evaluate the anti-transforming potential of CHK, tumor development was monitored in nude mice injected with MCF-7, MCF-7/neo and MCF-7/CHK cells, using standard laboratory techniques.

Tumor development in nude mice injected with MCF-7/CHK cells was significantly reduced (2/15) compared to tumor development in nude mice injected with control MCF-7 cells (15/15) or MCF-7/neo cells (12/15). These experiments suggest that overexpression of CHK can negatively regulate the growth of MCF-7 breast cancer cells in nude mice.

EXAMPLE 9: CHK OVEREXPRESSION AFFECTS S-PHASE ENTRY OF MCF-7 CELLS

A number of proto-oncogenes have been shown to affect cell cycle. Protoncogenes involved in the $G_0/G_1$ transition, such as myc and ras, are able to cooperate with cyclin $D_1$ in transforming cells. pp6osrc has been directly implicated in cell cycle regulation as well (Taylor, S. J., et al., *Bioassays*, 18:9–11 (1996), Roche, S., et al., *Science*, 269:1567–1569 (1995) ). Since it has been demonstrated that CHK can regulate pp6Osrc, it was investigated whether the level of CHK expression might modulate cell cycle kinetics using MCF-7 cells or transfected MCF-7 cells that overexpressed CHK protein (i.e., MCF-7/CHK). Growth-arrested postconfluent MCF-7, MCF-7/neo or MCF-7/CHK cells were obtained by serum depletion for 4 days. Cells were stimulated by 10% serum and harvested at specific times. These analyses indicate a significant delay in the entry to S-phase of the CHK transfected MCF07 cells compared to the controls. These results suggest that overexpression of CHK might have an effect on cell cycle.

EXAMPLE 10: EXPRESSION OF CHK USING THE VACCINE VIRUS/T7 RNA POLYMERASE HYBRID SYSTEM AND THE BACULOVIOUS SYSTEM

To analyze the interactions of CHK with ErbB-2, pp6osrc or other interacting molecules, a recombinant vaccinia virus was constructed to drive expression of CHK. CHK was inserted into a PTM-1 vaccinia recombinant plasmid under the control of the T7 RNA polymerase promoter. Recombinant viruses were selected, amplified and titered using standard techniques (Elroy-Stein, O., et al., *Proc. Natl. Acad. Sci. USA*, 87:6743–6747 (1990), Ausubel, F. M., et al., *CURRENT PROTOCOLS IN MOLECULAR BIOLOGY*, John Wiley & Son publishers (1992) ). To demonstrate that recombinant viruses produce appropriately immunoreactive proteins, MCF-7 cells were co-infected with the CHK recombinant vaccinia virus and the T7 polymerase recombinant virus at 10×MOI (multiplicity of infection) of each virus in 2.5% FCS DMEM. Cell lysates were run on SDS-PAGE and analyzed by immunoblotting with the anti-CHK antibodies. Expression of the 60 Kd immunoreactive CHK protein was demonstrated by immunoblotting with specific antibody. $^{35}$S-labeling of MCF-7 cells co-infected with the CHK recombinant vaccinia virus indicated that CHK is a major protein being synthesized in these cells.

To characterize the biochemical and functional properties of CHK, CHK has also been expressed using the baculovirus system. For baculovirus expression, CHK cDNA was inserted into a pAcHLT-ATm vector (PharMingen), as directed by the manufacturer. Recombinant CHK baculovirus was used to infect Sf9 insect cells for 72 hours at 5×MOI. Cell lysates were run on SDS-PAGE followed by Western blotting with anti-CHK antibody, or by protein staining of the gel with Coomassie Blue. Extracts of recombinant CHK baculovirus derived from infected Sf9 cells were chromatographed on phosphotyrosien-Affi-gel, DEAE-Sephacel, and Mono S. Purified CHK was eluted from these columns as described in Flink, N. A., et al., *J. Cell. Biochem.*, 55:389–397 (1994).

Figure 4:
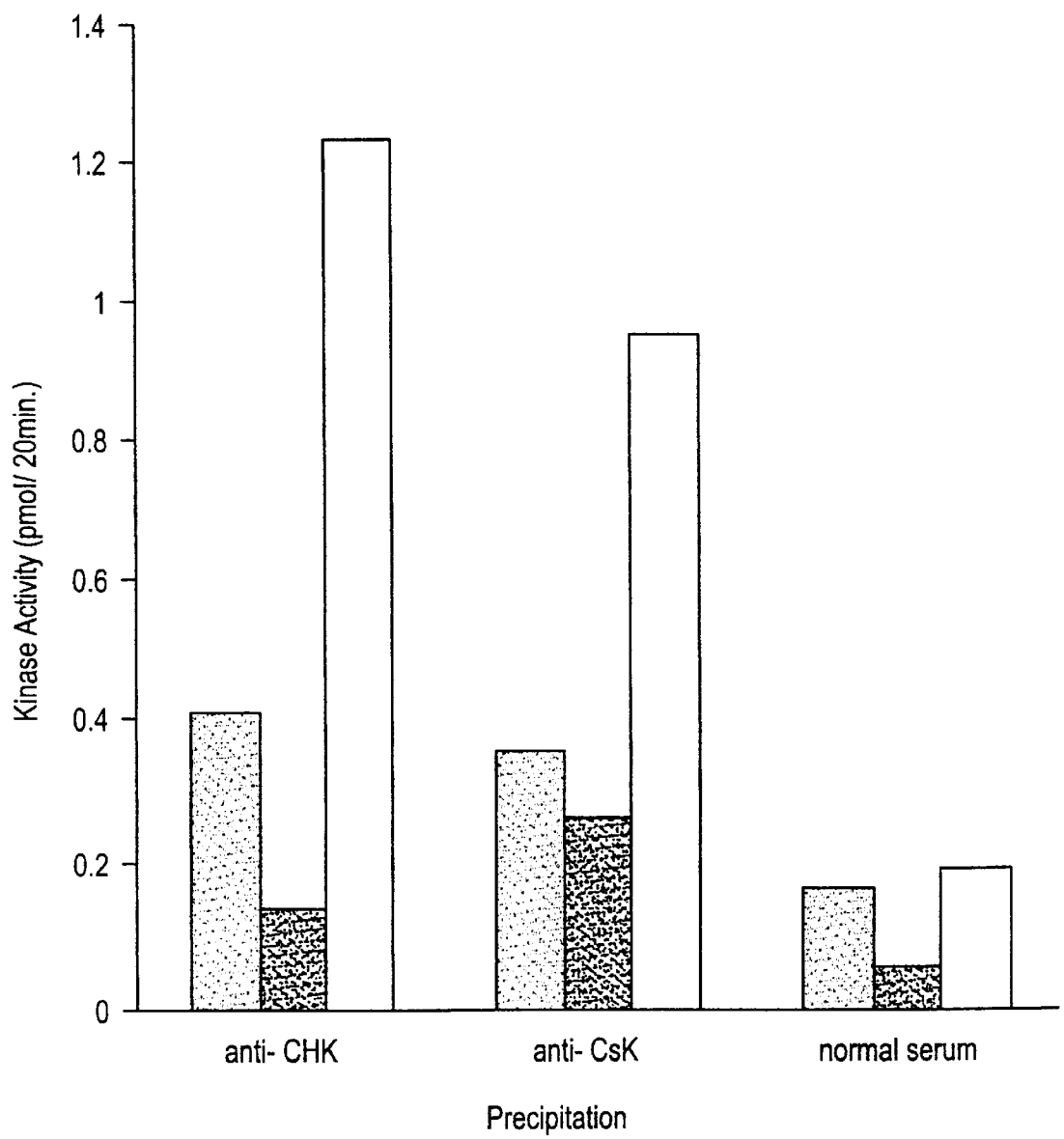
FIG. 4 is a graphic representation showing the results of an in vitro kinase assay of CHK and Csk immunoprecipitates.

EXAMPLE 11: CHK PHOSPHORYLATION OF THE C-TERMINAL src PEPTIDE, ENOLASE, AND POLY GLU/TYR In order to confirm the pp6osrc kinase as a substrate for CHK, immunoprecipitations of CHK and Csk from mouse brain were carried out. Mouse brain extracts were immunoprecipitated with either anti-CHK (murine Ctk), anti-Csk (murine), or normal mouse serum. Washed immunoprecipitates were used to phosphorylate substrates in the presence of 25 mM MOPS, pH 7.4, 50 $\mu$M Na$_3$ VO$_4$ 5 mM MnCl$_2$, 0.5 mM DTT, 125 $\mu$M $\gamma[^{32}p]$ ATP. Substrates tested were C-terminal src peptide, enolase, and Poly Glu/Tyr. Reactions were either terminated by the addition of SDS sample buffer (enolase, Poly Glu/Tyr) and run on SDS-PAGE, or terminated by pipetting onto P81 paper (src peptide) and washed extensively in 75 mM phosphoric acid. In vitro kinase assays of CHK and Csk immunoprecipates showed that both kinases phosphoylated the C-terminal scr peptide, enolase and poly Glu/Try to similar degrees (FIG. 4).

=Poly Glu/Tyr; ■=Enolase; ⧉=RC-terminal src peptide.

EQUIVALENTS

Those skilled in the art will recognize, or be able to ascertain using no more than routine experimentation, many equivalents to the specific embodiments of the invention described herein. Such equivalents are intended to be encompassed by the following claims.

---

We claim:

1. A method of detecting the presence of cancer in mammalian breast tissue comprising detecting the expression of Csk Homologous Kinase in breast rissue wherein the detection of the expression of Csk Homologous Kinase is indicative of cancer, wherein the Csk Homologous Kinase comprises SEQ ID NO 2 or SEQ ID NO 4.

2. The method of claim 1 wherein the expression of Csk Homologous Kinase is detected by immunohistochemical staining of breast biopsy tissue with anti-Csk Homologous Kinase antibodies.

3. The method of claim 2 wherein the anti-Csk Homologous Kinase antibodies specifically bind to the Csk Homologous Kinase protein or a fragment of the Csk Homologous Kinase protein.

* * * * *

UNITED STATES PATENT AND TRADEMARK OFFICE
CERTIFICATE OF CORRECTION

PATENT NO.    : 5,981,201
DATED         : November 9, 1999
INVENTOR(S)   : Hava Avraham and Jerome E. Groopman It is certified that error appears in the above-identified patent and that said Letters Patent is hereby corrected as shown below:

In the Sequence Listing, under "(1) General Information," change "(iii) NUMBER OF SEQUENCES: 9" to -- (iii) NUMBER OF SEQUENCES: 5, --.

In SEQ ID NO: 2, between amino acid residue 77 "Ile" and 79 "Glu" insert -- Leu --; After amino acid residue 79 "Glu", delete "Leu Glu Ala" and insert -- Ala --.

In SEQ ID NO: 4 change amino acid residue 3 "Ser" to -- Ile -- and change amino acid a residue 12 "Ser" to -- Ile --.

Claims,
Claim 1,
Line 3, replace "reisse" with -- tissue --.

Signed and Sealed this

Twenty-third Day of October, 2001

Attest:

NICHOLAS P. GODICI
Attesting Officer    Acting Director of the United States Patent and Trademark Office

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 1987 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
GGAGCAACTC GCTCCAAGTT GTGCAGCCGG GACCGCCTCG GGGTGTGCAG CCGGCTCGCG      60

GAGGCCCTCC TGGGGCGGG CGGGGCGCGG CTCGGGGCG CCCCCTGAGC AGAAAACAGG      120

AAGAACCAGG CTCGGTCCAG TGGCACCCAG CTCCCTACCT CCTGTGCCAG CCGCCTGGCC     180

TGTGGCAGGC CATTCCCAGC GTCCCCGACT GTGACCACTT GCTCAGTGTG CCTCTCACCT    240

GCCTCAGTTT CCTCTGGGGG CGATGGCGGG GCGAGGCTCT CTGGTTTCCT GGCGGGCATT    300

TCACGGCTGT GATTCTGCTG AGGAACTTCC CCGGGTGAGC CCCCGCTTCC TCCGAGCCTG    360
```

```
GCACCCCCCT CCCGTCTCAG CCAGGATGCC AACGAGGCGC TGGGCCCCGG GCACCCAGTG    420

TATCACCAAA TGCGAGCACA CCCGCCCCAA GCCAGGGGAG CTGGCCTTCC GCAAGGGCGA    480

CGTGGTCACC ATCCTGGAGG CCTGCGAGAA CAAGAGCTGG TACCGCGTCA AGCACCACAC    540

CAGTGGACAG GAGGGCTGC TGGCAGCTGG GGCGCTGCGG GACGGGGAGG CCCTCTCCGC     600

AGACCCCAAG CTCAGCCTCA TGCCGTGGTT CCACGGGAAG ATCTCGGGCC AGGAGGCTGT    660

CCAGCAGCTG CAGCCTCCCG AGGATGGGCT GTTCCTGGTG CGGGAGTCCG CGCGCCACCC    720

CGGCGACTAC GTCCTGTGCG TGAGCTTTGG CCGCGACGTC ATCCACTACC GCGTGCTGCA    780

CCGCGACGGC CACCTCACAA TCGATGAGGC CGTGTTCTTC TGCAACCTCA TGGACATGGT    840

GGAGCATTAC AGCAAGGACA AGGGCGCTAT CTGCACCAAG CTGGTGAGAC AAAGCGGAA     900

ACACGGGACC AAGTCGGCCG AGGAGGAGCT GGCCAGGGCG GGCTGGTTAC TGAACCTGCA    960

GCATTTGACA TTGGGAGCAC AGATCGGAGA GGGAGAGTTT GGAGCTGTCC TGCAGGGTGA    1020

GTACCTGGGG CAAAAGGTGG CCGTGAAGAA TATCAAGTGT GATGTGACAG CCCAGGCCTT    1080

CCTGGACGAG ACGGCCGTCA TGACGAAGAT GCAACACGGA AACCTGGTGC GTCTCCTGGG    1140

CGTGATCCTG CACCAGGGGC TGTACATTGT CATGGAGCAC GTGAGCAAGG CAACCTGGT    1200

GAACTTTCTG CGGACCCGGG GTCGAGCCCT CGTGAACACC GCTCAGCTCC TGCAGTTTTC    1260

TCTGCACGTG GCCGAGGGCA TGGAGTACCT GGAGAGCAAG AAGCTTGTGC ACCGCGACCT    1320

GGCCGCCCGC AACATCCTGG TCTCAGAGGA CCTGGTGGCC AAGGTCAGCG ACTTTGGCCT    1380

GGCCAAAGCC GAGCGGAAGG GGCTAGACTC AAGCCGGCTG CCCGTCAAGT GGACGGCGCC    1440

CGAGGCTCTC AAACACGGGT TCACCAGCAA GTCGGATGTC TGGAGTTTTG GGGTGCTGCT    1500

CTGGGAGGTC TTCTCATATG GACGGGCTCC GTACCCTAAA ATGTCACTGA AGAGGTGTC    1560

GGAGGCCGTG GAGAAGGGGT ACCGCATGGA ACCCCCGAG GGCTGTCCAG CCCCGTGCA     1620

CGTCCTCATG AGCAGCTGCT GGGAGGCAGA GCCGCCCGCC GGCCACCCTT CCGCAAACTG    1680

GCCGAGAAGC TGGCCCGGGA GCTACGCAGT GCAGGTGCCC CAGCCTCCGT CTCAGGGCAG    1740

GACGCCGACG GTCCACCTCG CCCCGAAGCC AGGAGCCCTG ACCCCACCCG GTGGCCCTTG    1800

GCCCCAGAGG ACCGAGAGAG TGGAGAGTGC GGCGTGGGGG CACTGACCAG GCCCAAGGAG    1860

GGTCCAGGCG GGCAAGTCAT CCTCCTGGTG CCCACAGCAG GGGCTGGCCC ACGTAGGGGG    1920

CTCTGGGCGG CCCGTGGACA CCCCAGACCT GCGAAGGATG ATCGCCCGAT AAAGACGGAT    1980

TCTAAGG                                                              1987
```

(2) INFORMATION FOR SEQ ID NO:2:

(i) SEQUENCE CHARACTERISTICS:
        (A) LENGTH: 528 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

```
Met Ala Gly Arg Gly Ser Leu Val Ser Trp Arg Ala Phe His Gly Cys
 1               5                  10                  15

Asp Ser Ala Glu Glu Leu Pro Arg Val Ser Pro Arg Phe Leu Arg Ala
            20                  25                  30

Trp His Pro Pro Pro Val Ser Ala Arg Met Pro Thr Arg Arg Trp Ala
        35                  40                  45
```

-continued

```
Pro Gly Thr Gln Cys Ile Thr Lys Cys Glu His Thr Arg Pro Lys Pro
    50                  55                  60
Gly Glu Leu Ala Phe Arg Lys Gly Asp Val Val Thr Ile Glu Leu Glu
65                  70                  75                  80
Ala Cys Glu Asn Lys Ser Trp Tyr Arg Val Lys His His Thr Ser Gly
                85                  90                  95
Gln Glu Gly Leu Leu Ala Ala Gly Ala Leu Arg Asp Gly Glu Ala Leu
                100                 105                 110
Ser Ala Asp Pro Lys Leu Ser Leu Met Pro Trp Phe His Gly Lys Ile
            115                 120                 125
Ser Gly Gln Glu Ala Val Gln Gln Leu Gln Pro Pro Glu Asp Gly Leu
    130                 135                 140
Phe Leu Val Arg Glu Ser Ala Arg His Pro Gly Asp Tyr Val Leu Cys
145                 150                 155                 160
Val Ser Phe Gly Arg Asp Val Ile His Tyr Arg Val Leu His Arg Asp
                165                 170                 175
Gly His Leu Thr Ile Asp Glu Ala Val Phe Phe Cys Asn Leu Met Asp
                180                 185                 190
Met Val Glu His Tyr Ser Lys Asp Lys Gly Ala Ile Cys Thr Lys Leu
            195                 200                 205
Val Arg Pro Lys Arg Lys His Gly Thr Lys Ser Ala Glu Glu Glu Leu
    210                 215                 220
Ala Arg Ala Gly Trp Leu Leu Asn Leu Gln His Leu Thr Leu Gly Ala
225                 230                 235                 240
Gln Ile Gly Glu Gly Glu Phe Gly Ala Val Leu Gln Gly Glu Tyr Leu
                245                 250                 255
Gly Gln Lys Val Ala Val Lys Asn Ile Lys Cys Asp Val Thr Ala Gln
                260                 265                 270
Ala Phe Leu Asp Glu Thr Ala Val Met Thr Lys Met Gln His Glu Asn
            275                 280                 285
Leu Val Arg Leu Leu Gly Val Ile Leu His Gln Gly Leu Tyr Ile Val
    290                 295                 300
Met Glu His Val Ser Lys Gly Asn Leu Val Asn Phe Leu Arg Thr Arg
305                 310                 315                 320
Gly Arg Ala Leu Val Asn Thr Ala Gln Leu Leu Gln Phe Ser Leu His
                325                 330                 335
Val Ala Glu Gly Met Glu Tyr Leu Glu Ser Lys Lys Leu Val His Arg
                340                 345                 350
Asp Leu Ala Ala Arg Asn Ile Leu Val Ser Glu Asp Leu Val Ala Lys
            355                 360                 365
Val Ser Asp Phe Gly Leu Ala Lys Ala Glu Arg Lys Gly Leu Asp Ser
    370                 375                 380
Ser Arg Leu Pro Val Lys Trp Thr Ala Pro Glu Ala Leu Lys His Gly
385                 390                 395                 400
Phe Thr Ser Lys Ser Asp Val Trp Ser Phe Gly Val Leu Leu Trp Glu
                405                 410                 415
Val Phe Ser Tyr Gly Arg Ala Pro Tyr Pro Lys Met Ser Leu Lys Glu
                420                 425                 430
Val Ser Glu Ala Val Glu Lys Gly Tyr Arg Met Glu Pro Glu Gly
            435                 440                 445
Cys Pro Gly Pro Val His Val Leu Met Ser Ser Cys Trp Glu Ala Glu
    450                 455                 460
Pro Pro Ala Gly His Pro Ser Ala Asn Trp Pro Arg Ser Trp Pro Gly
```

```
465                 470                 475                 480
Ser Tyr Ala Val Gln Val Pro Gln Pro Pro Ser Gln Gly Arg Thr Pro
                485                 490                 495
Thr Val His Leu Ala Pro Lys Pro Gly Ala Leu Thr Pro Pro Gly Gly
            500                 505                 510
Pro Trp Pro Gln Arg Thr Glu Arg Val Glu Ser Ala Ala Trp Gly His
        515                 520                 525
```

(2) INFORMATION FOR SEQ ID NO:3:

(i) SEQUENCE CHARACTERISTICS:
        (A) LENGTH: 147 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
GGATCCATTC ACAGAGACCT AGCAGCACGC AACATCCTGG TCTCAGAGGA CCTGGTAACC      60

AAGGTCAGCG ACTTTGGCCT GGCCAAAGCC GAGCGGAAGG GGCTAGACTC AAGCCGGCTG     120

CCCGTCAAAT GGATGGCTCC CGAATTC                                        147
```

(2) INFORMATION FOR SEQ ID NO:4:

(i) SEQUENCE CHARACTERISTICS:
        (A) LENGTH: 49 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:4:

```
Gly Ser Ser His Arg Asp Leu Ala Ala Arg Asn Ser Leu Val Ser Glu
 1               5                  10                  15
Asp Leu Val Thr Lys Val Ser Asp Phe Gly Leu Ala Lys Ala Glu Arg
             20                  25                  30
Lys Gly Leu Asp Ser Ser Arg Leu Pro Val Lys Trp Met Ala Pro Glu
         35                  40                  45
Phe
```

(2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Asp Tyr Lys Asp Asp Asp Asp Lys
 1               5
```

(2) INFORMATION FOR SEQ ID NO:6:

(i) SEQUENCE CHARACTERISTICS:
        (A) LENGTH: 10 amino acids
        (B) TYPE: amino acid
        (C) STRANDEDNESS: single
        (D) TOPOLOGY: linear

```
    (ii) MOLECULE TYPE: peptide (ix) FEATURE:
         (A) NAME/KEY: Other
         (B) LOCATION: 5...5
         (D) OTHER INFORMATION: Xaa = phosphotyrosine (xi) SEQUENCE DESCRIPTION: SEQ ID NO:6:

Glu Asn Pro Glu Xaa Leu Gly Leu Asp Val
1               5                   10

(2) INFORMATION FOR SEQ ID NO:7:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Other
         (B) LOCATION: 4...5
         (D) OTHER INFORMATION: Xaa = phosphotyrosine (xi) SEQUENCE DESCRIPTION: SEQ ID NO:7:

Asp Asn Leu Xaa Xaa Trp Asp Glu Asn Ser
1               5                   10

(2) INFORMATION FOR SEQ ID NO:8:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Other
         (B) LOCATION: 4...4
         (D) OTHER INFORMATION: Xaa = phosphotyrosine (xi) SEQUENCE DESCRIPTION: SEQ ID NO:8:

Glu Pro Glu Xaa Val Asn Glu Ser Glu
1               5

(2) INFORMATION FOR SEQ ID NO:9:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Other
         (B) LOCATION: 4...4
         (D) OTHER INFORMATION: Xaa = phosphotyrosine (xi) SEQUENCE DESCRIPTION: SEQ ID NO:9:

Ala Glu Glu Xaa Leu Val Pro Glu Glu
1               5
```